United States Patent [19]

Grayson et al.

[11] 4,421,921
[45] Dec. 20, 1983

[54] PROCESS FOR THE PRODUCTION OF 3-PICOLINE

[75] Inventors: James I. Grayson, Visp; Rolf Dinkel, Münchenstein, both of Switzerland

[73] Assignee: Lonza Ltd., Gampel, Switzerland

[21] Appl. No.: 415,835

[22] Filed: Sep. 8, 1982

[30] Foreign Application Priority Data

Sep. 29, 1981 [CH] Switzerland .......................... 6250/81

[51] Int. Cl.³ .................. C07D 213/09; C07D 213/12; C07D 213/10
[52] U.S. Cl. .................................................... 546/251
[58] Field of Search ......................................... 546/251

[56] References Cited

U.S. PATENT DOCUMENTS 4,337,342  6/1982  Dinkel .................................. 546/251

Primary Examiner—Robert T. Bond
Attorney, Agent, or Firm—Fisher, Christen & Sabol

[57] ABSTRACT

Process for the production of 3-picoline. Acrolein or a mixture of acrolein and formaldehyde is reacted in a liquid aqueous phase at a temperature of 180° to 280° C. in a closed vessel. Ammonia and/or ammonium ions, and anions of an inorganic or organic acid, which has an acid dissociation constant of $10^6$ to $10^{-12}$, at 20° C., are also present.

13 Claims, No Drawings

PROCESS FOR THE PRODUCTION OF 3-PICOLINE

BACKGROUND OF THIS INVENTION

1. Field Of This Invention

This invention relates to a process for the production of 3-picoline.

2. Prior Art

Pyridine bases are important intermediate products in the chemical industry, for example, used in the production of nicotinic acid or nicotinic acid amide. Various processes are known for the production of pyridine bases.

2-methyl-5-ethylpyridine is produced industrially today in a fluid-phase process from acetaldehyde or paraldehyde and ammonia in the presence of very diverse catalysts, such as, ammonium salts. Small quantities of 2- and 4-picoline are obtained as by-products. 2- and 4-picoline are produced today in gas-phase reactions at a temperature of about 400° C. from acetaldehyde and ammonia with the use of solid bed or fluid bed catalysts, based on alumimum silicate.

For the production of pyridine as well as 3-picoline, which continuously increases in importance, gas-phase reactions are used today. The formation of 2- and 4-picoline is suppressed in favor of 3-picoline by means of the addition of formaldehyde to the acetaldehyde. Such reaction also takes place in a solid bed or fluid bed, with aluminum silicate as the catalyst at a temperature of about 400° C. According to such processes, yields of 3-picoline in the order of at most 40 to 44 percent are achieved. Besides, large quantities of pyridine are obtained.

It is also known that, instead of starting with saturated aldehydes, one can start out from unsaturated aldehydes, for example, acrolein or crotonaldehyde. Such reactions take place in the gaseous phase at a high temperature. The yields are essentially equally as high as or are somewhat lower than when saturated aldehydes are used as the starting material (see German OS No. 22 39 801).

It is further known to react acrolein with an ammonium salt of an organic acid, for example, acetic acid, in an acid reaction medium at a relatively low temperature (15° to 150° C.). The yields of 3-picoline are relatively low (see British Patent No. 1,240,928).

BROAD DESCRIPTION OF THIS INVENTION

An object of this invention is to provide a process for producing 3-picoline at higher yields than the above prior art with the suppression of the formation of pyridine as much as possible. Another object of this invention is to provide a composition from which 3-picoline is provided. Other objects and advantages of this invention are set out herein or are obvious herefrom to one ordinarily skilled in the art.

The objects and advantages of this invention are achieved by the process of this invention.

This invention involves a process for producing 3-picoline. The process involves reacting acrolein, or a mixture of acrolein and formaldehyde, or a mixture of acrolein, formaldehyde and acetaldehyde in the fluid, aqueous phase at a temperature of 180° to 280° C. in a closed vessel. Ammonia and/or ammonium ions are present. The anions of an inorganic and/or organic acid, which has an acid dissociation constant of $10^6$ to $10^{-12}$ at 20° C., are also present.

Acetaldehyde, as used within the scope of this invention, includes its polymers, for example, paraldehyde.

In order to include the anions of inorganic and/or organic acids, which are important for the reaction, and which have an acid dissociation constant of $10^6$ to $10^{-12}$ at 20° C., the corresponding water-soluble alkali and/or ammonium salts of the acids are added to the reaction solution. Examples of salts of the acids, within the scope of this invention are, for example, the sodium, potassium or ammonium salts of pentaboric acid (such as ammonium pentaborate), carbonic acid (such as ammonium carbonate), phosphoric acid (such as potassium dihydrogen phosphate, ammonium dihydrogen phosphate, dipotassium hydrogen phosphate or diammonium hydrogen phosphate), sulfuric acid (such as sodium hydrogen sulfate or ammonium sulfate), hydrofluoric acid (such as sodium fluoride, ammonium fluoride or ammonium hydrogen difluoride), hydrochloric acid (such as ammonium chloride), hydrobromic acid (such as ammonium bromide), heptamolybdenic acid (such as ammonium heptamolybdate), formic acid (such as ammonium formate), acetic acid (such as sodium acetate or ammonium acetate), propionic acid (such as ammonium proprionate), butyric acid (such as ammonium butyrate), succinic acid (such as disodium succinate or diammonium succinate), adipic acid (such as diammonium adipinate), benzoic acid (such as sodium benzoate or ammonium benzoate), phthalic acid (such as diammonium phthalate), terephthalic acid (such as diammonium terephthalate), nicotinic acid (such as ammonium nicotinate) and isonicotinic acid (such as ammonium isonicotinate).

For the formation of 3-picoline from acrolein or a mixture of acrolein and formaldehyde or a mixture of acrolein, formaldehyde and acetaldehyde, the presence of ammonia and/or ammonium ions are necessary. Whenever ammonia is used, and the ammonia is to be inserted either in gaseous form or as an aqueous solution, such is sufficient whenever alkali salts of the cited acids are used. However, mixtures of alkali salts and ammonium salts can also be used. Whenever ammonia as such is not used, then ammonium salts or mixtures of ammonium salts and alkali salts are used. Whenever liquid starting materials which are not miscible with one another (such as, paraldehyde together with aqueous formaldehyde) are used, then it is advantageous to use a small quantity of an homogenizing agent, such as an alcohol or cyclic ether, for homogenization, or to feed the non-miscible liquid starting materials by means of a separate pump into the reactor.

According to the process of this invention, 3-picoline is surprisingly obtained in yields up to about 58.5 percent and the formation of pyridine is largely suppressed (below 2 percent). 3-ethylpyridine as well as small quantities of 2,5-dimethylpyridine, 3,5-dimethylpyridine and 2-methyl-5-ethylpyridine are obtained as by-products.

Whenever acrolein and formaldehyde are used together, the process is effectively carried out at a mole ratio between 1 to 0 (or 0.01) and 1 to 0.5. Whenever acrolein, formaldehyde and acetaldehyde are reacted, then the mole ratio of acrolein to formaldehyde is between 1 to 0.3 and 1 to 3, and the mole ratio acrolein to acetaldehyde is between 1 to 0.6 and 1 to 4.

The reaction temperature is advantageously 180° to 280° C., effectively 205° to 240° C., and preferably 205° to 230° C. The reaction is carried out in the liquid phase (aqueous phase) under a pressure which occurs in the case of the reaction in the closed vessel at a predetermined temperature. It is advantageous to stir the reaction batch during the reaction.

The quantity of ammonia and/or ammonium ions used is 0.5 to 3 mole of ammonia and/or ammonium ions per mole of educt, advantageously 0.5 to 2.0 moles per mole of educt. The quantity of the anions of inorganic and/or organic acids used is advantageously 0.1 to 3 mole, preferably 0.2 to 1.0 mole, per mole of educt. The starting pH value of the aqueous solution advantageously is between 5.0 and 12.5.

The addition of the aldehyde is accomplished effectively according to the measure of its consumption. Thus it is favorable, for example, in the case of working in a 2-liter container and the use of 350 ml of aldehyde, to add it continuously over a 20 to 90 minute period. In the case of other conditions, one must select the corresponding addition times.

At the end of the desired reaction period, the temperature is lowered to ambient temperature and the 3-picoline is obtained in a known manner from the reaction mixture. One method involves first bringing the pH value of the water phase into the basic area and then extracting the organic material from the aqueous reaction mixture with an organic solvent, for example, benzene, toluene, xylene, methylene chloride, chloroform, ether, etc. The organic solvent is then evaporated and 3-picoline is obtained by fractional distillation. Within the scope of this invention, any other methods for the separating and obtaining of the product can also be used.

One advantage of the process of this invention is also that the aqueous phase obtained after the extraction of the reaction mixture with an organic solvent, after re-enrichment with ammonia and/or ammonium ions, can be returned into the reactor. The aqueous salt phase is composed of the water originally present in the salt solution, the unreacted quantity of ammonia and/or ammonium salt, the optionally present metal salt, and the liberated acid of the ammonium salt participating in the reaction, as well as of one mole of water for every mole of the educt consumed during the reaction. Therefore, the aqueous salt phase is concentrated with the help of any known process, for example, by evaporation, in order to remove the water formed as a consequence of the condensation reaction. A re-enrichment of ammonia and/or ammonium salt can then be achieved by inserting gaseous ammonia at ambient temperature into the aqueous solution, with re-formation of the ammonium salt from the acid, if such is present.

Although the invention has been described as a discontinuous process, the process can also be continuously operated within the scope of this invention. In the case of an embodiment of a continuous process, the reaction participants are continuously introduced into a suitable pressure reactor from which the reaction mixture is continuously drawn off. The reaction products are separated from this, the aqueous salt phase is concentrated and unchanged reaction participants are then again made up and returned to the reaction vessel. The continuous process can be carried out in any reactor which permits an intimate mixing of the reaction participants with violent stirring, for example, in a continuously stirred tank reactor.

This invention also includes a composition containing (a) acrolein or a mixture of acrolein and formaldehyde in the liquid aqueous phase, (b) ammonia and/or ammonium ions, and (c) anions of an organic acid, which has an acid dissociation constant of $10^6$ to $10^{-12}$ at 20° C.

By way of summary, this invention involves a process for the production of 3-picoline from acrolein or a mixture of acrolein and formaldehyde or a mixture of acrolein, formaldehyde and acetaldehyde in the aqueous phase.

DETAILED DESCRIPTION OF THIS INVENTION

As used herein, all parts, percentages, ratios and proportions are on a weight basis unless otherwise stated herein or otherwise obvious herefrom to one ordinarily skilled in the art.

EXAMPLE 1

1140 ml of a 3.40 molar aqueous solution of diammonium hydrogen phosphate (pH 8.3) was heated in a 2-liter autoclave to 205° C. and was stirred at 1500 rpm. A mixture of 115.0 g of acrolein and 100.0 of ethanol was pumped continuously into this solution over a 31 minute period. At the same time the reaction pressure varied between 20 and 24 bar. After completion of the addition of the educt mixture, the reaction mass continued to be stirred for 20 minutes at 205° C. and was then cooled down to ambient temperature. Finally, an extraction was made three times, each with 100 ml of methylene chloride. A gas chromatographic analysis of the combined methylene chloride extracts was made. The following products resulted in the following yields, related to the amount of acrolein used: pyridine, 0.7 percent; 3-picoline, 50.7 percent; 3-ethylpyridine, 5.7 percent; 2,5-lutidine, 0.6 percent; and 3,5-lutidine, 1.0 percent.

EXAMPLE 2

1140 ml of a 3.40 molar aqueous solution of diammonium hydrogen phosphate (pH 8.3) was heated in a 2-liter autoclave to 230° C. and was stirred at 1500 rpm. 115.0 g of acrolein was pumped continuously into this solution over a 24 minute period. At the same time the reaction pressure varied between 32 and 33 bar. After completion of the addition of the educt mixture, the reaction mass continued to be stirred for 10 minutes at 230° C. and was then cooled at ambient temperature. Finally, an extraction was made three times, each with 100 ml of methylene chloride. A gas chromatographic analysis of the combined methylene chloride extracts was made. The following products resulted in the following yields, related to the amount of acrolein used: pyridine, 0.9 percent; 3-picoline, 52.4 percent; 3-ethylpyridine, 7.6 percent; 2,5-lutidine, 0.1 percent; 3,5-lutidine, 0.6 percent; 2-methyl-5-ethylpyridine, 0.3 percent.

Concerning Examples 3 to 7, the following note deals with the calculation of the yields therein. Whenever the reaction was carried out with the starting materials acetaldehyde (or paraldehyde) and/or formaldehyde and acrolein, 1 mole of acrolein was counted as 1 mole of acetaldehyde plus 1 mole of formaldehyde, and the yields were related to the total amount of acetaldehyde (A) used, or the total amount of formaldehyde (F) used.

EXAMPLE 3

1140 ml of a 3.40 molar aqueous solution of diammonium hydrogen phsophate (pH 8.5) was heated in a 2-liter autoclave to 230° C. and was stirred at 1500 rpm. A mixture of 31.3 g of acrolein, 93.3 g of acetaldehyde and 161.8 g of a 30.1 percent formaldehyde solution was continuously pumped into the autoclave over a 54 minute period. (The mole ratio of acrolein to acetaldehyde to formaldehyde was 1 to 4 to 3.) At the same time, the reaction pressure varied between 31 and 32 bar. After completion of the addition of the educt mixture, the reaction mass continued to be stirred for 10 minutes at 230° C. and was then cooled down to room temperature. Finally, an extraction was made three times, each with 100 ml of methylene chloride. A gas chromatographic analysis of the combined methylene chloride extracts was made. The following products resulted in the following yields, always related to the amount of the aldehyde involved: pyridine, 0.9 percent (A); 3-picoline, 56.6 percent (F); 3-ethylpyridine, 24.7 percent (A); 2,5-lutidine, 3.4 percent (A); 3,5-lutidine, 0.7 percent (F); and 2-methyl-5-ethylpyridine, 1.6 percent (A).

EXAMPLE 4

Example 3 was repeated using the same conditions and procedure, unless otherwise indicated (temperature, 230° C.; dosing time, 48 minutes; reaction pressure, 32 to 35 bar). 31.3 g of acrolein, 96.0 g of paraldehyde, 160.7 g of a 30.3 percent formaldehyde solution and 50.0 g of ethanol were used. The mole ratio of acrolein to acetaldehyde to formaldehyde was 1 to 4 to 3. The following products were produced in the following yields, related to the amount of the aldehyde involved: pyridine, 1.0 percent (A); 3-picoline, 54.6 percent (F); 3-ethylpyridine, 20.3 percent (A); 2,5-lutidine, 3.8 percent (A); 3,5-lutidine, 0.7 percent (F); and 2-methyl-5-ethylpyridine, 2.5 percent (A).

EXAMPLE 5

Example 3 was repeated using the same conditions and procedure, unless otherwise indicated (temperature, 230° C.; dosing time, 48 minutes; reaction pressure, 32 to 36 bar). 62.6 g of acrolein, 72.0 g of paraldehyde, 108.2 g of a 30.3 percent formaldehyde solution and 50.0 g of ethanol were used. The mole ratio of acrolein to acetaldehyde to formaldehyde was 1 to 1.5 to 1. The following products were produced in the following yields, related to the amount of the aldehyde involved: pyridine, 1.4 percent (A); 3-picoline, 56.7 percent (F); 3-ethylpyridine, 23.7 percent (A); 2,5-lutidine, 4.2 percent (A); 3,5-lutidine, 0.8 percent (F); and 2-methyl-5-ethylpyridine, 3.0 percent (A).

EXAMPLE 6

Example 3 was repeated using the same conditions and procedure, unless otherwise indicated (temperature, 230° C.; dosing time, 34 minutes; reaction pressure, 32 to 35 bar). 95.4 g of acrolein, 47.5 g of paraldehyde, 54.7 g of a 30.3 percent formaldehyde solution and 50.0 g of ethanol were used. The mole ratio of acrolein to acetaldehyde to formaldehyde was 3 to 2 to 1. The following products were produced in the following yields, related to the amount of the aldehyde involved: pyridine, 1.5 percent (A); 3-picoline, 54.5 percent (F); 3-ethylpyridine, 22.9 percent (A); 2,5-lutidine, 3.6 percent (A); 3,5-lutidine, 0.8 percent (F) and 2-methyl-5-ethylpyridine, 2.8 percent (A).

EXAMPLE 7

Example 3 was repeated using the same conditions and procedure, unless otherwise indicated (temperature, 230° C.; dosing time, 42 minutes; reaction pressure, 32 to 34 bar). 125.2 g of acrolein, 52.9 g of a 30.1 percent formaldehyde solution and 20.0 g of ethanol were used. The mole ratio of acrolein to formaldehyde was 4 to 1. The following products were produced in the following yields, related to the amount of the aldehyde involved: pyridine, 0.5 percent (A); 3-picoline, 53.3 percent (A); 3-ethylpyridine, 2.3 percent (A); 2,5-lutidine, 0.3 percent (A); and 3,5-lutidine, 1.5 percent (F).

EXAMPLE 8

1140 ml of a 3.40 molar aqueous solution of ammonium acetate (pH 7.8) was heated to 230° C. in a 2-liter autoclave and was stirred at 1500 rpm. A mixture of 115.0 g of acrolein and 100.0 of ethanol was continuously pumped into the solution over a 57 minute period. At the same time the reaction pressure varied between 26 and 30 bar. After completion of the addition of the educt mixture, the reaction mass continued to be stirred for 10 minutes at 230° C. and was then cooled to ambient temperature. Finally, an extraction was made three times, each with 100 ml of methylene chloride. A gas chromatographic analysis of the combined methylene chloride extracts was made. The following products were produced in the following yields, related to the amount of acrolein used: pyridine, 0.8 percent; 3-picoline, 36.3 percent; 3-ethylpyridine, 6.9 percent; 2,5-lutidine, 0.6 percent; 3,5-lutidine, 0.8 percent and 2-methyl-5-ethylpyridine, 0.3 percent.

EXAMPLE 9

A solution of 397.1 g of dipotassium hydrogen phosphate in 1140 ml of 2.5 molar aqueous ammonia (pH 12.1) was heated in a 2-liter autoclave to 230° C. and was stirred at 1500 rpm. A mixture of 115.0 of acrolein and 100.0 g of ethanol was continuously pumped into the solution over a 67 minute period. At the same time the reaction pressure varied between 35 and 38 bar. After completion of the addition of the educt mixture, the reacted mass continued to be stirred for 10 minutes at 230° C. and was then cooled to ambient temperature. Finally, an extraction was made three times, each with 100 ml of methylene chloride. A gas chromatographic analysis of the combined methylene chloride extracts was made. The following products were produced in the following yields, related to the amount of acrolein used: pyridene, 1.4 percent; 3-picolene, 58.4 percent; 3-ethylpyridene, 4.8 percent; 2,5-lutidine, 1.2 percent, 3,5-lutidine, 3.1 percent; and 2-methyl-5-ethylpyridine, 1.0 percent.

EXAMPLE 10

A solution of 137.0 g of sodium hydrogen sulfate monohydrate in 1140 ml of 4.0 molar aqueous ammonia (pH 10.9) was heated in a 2-liter autoclave to 230° C. and was stirred at 1500 rpm. A mixture of 115.0 g of acrolein and 100.0 g of ethanol was continuously pumped into the solution over a 38 minute period. At the same time the reaction pressure varied between 35 and 37 bar. After completion of the addition of the educt mixture, the reaction mass continued to be stirred for 10 minutes at 230° C. and was then cooled to ambient temperature. Finally, an extraction was made three times, each with 100 ml of methylene chloride. A gas chromatographic analysis of the combined methylene chloride extracts was made. The following products were produced in the following yields, related to the amount of acrolein used: pyridine, 1.9 percent; 3-picoline, 56.1 percent; 3-ethylpyridine, 6.1 percent, 2,5-lutidine, 1.5 percent; 3,5-lutidine, 1.1 percent; and 2-methyl-5-ethylpyridine, 0.2 percent.

What is claimed is:

1. Process for the production of 3-picoline comprising reacting acrolein or a mixture of acrolein and formaldehyde in the liquid aqueous phase at a temperature of 180° to 280° C. in a closed vessel in the presence of ammonia and/or ammonium ions and in the presence of anions of an inorganic and/acid or organic acid, which has an acid dissociation constant of $10^6$ to $10^{-12}$ at 20° C.

2. Process as claimed in claim 1 wherein a mixture of acrolein and formaldehyde is reacted together with acetaldehyde.

3. Process as claimed in claim 1 wherein the mixture of acrolein and formaldehyde has a mole ratio between 1 to 0 and 1 to 0.5.

4. Process as claimed in claim 1 or 2 wherein a mixture of acrolein, formaldehyde and acetaldehyde is used, and such mixture has a mole ratio of acrolein to formaldehyde between 1 to 0.3 and 1 to 3 and has a mole ratio of acrolein to acetaldehyde between 1 to 0.6 and 1 to 4.

5. Process as claimed in claim 4 wherein the acetaldehyde is used in the form of one of its derivatives.

6. Process as claimed in claim 4 wherein the anion of the organic and/or inorganic acid are inserted into the reaction solution by means of the addition of the corresponding water soluble alkali and/or ammonium salt.

7. Process as claimed in claim 6 wherein the salt is used in an aqueous solution at a concentration of 0.3 to 10 mole/liter.

8. Process as claimed in claim 4 wherein the temperature is 205° to 230° C.

9. Composition comprised of (a) acrolein or a mixture of acrolein and formaldehyde in the liquid aqueous phase, (b) ammonia and/or ammonium ions, and (c) anions of an organic acid, which has an acid dissociation constant of $10^6$ to $10^{-12}$ at 20° C.

10. Composition as claimed in claim 9 wherein acetaldehyde is also present.

11. Composition as claimed in claim 10 wherein the mole ratio of acrolein to formaldehyde is between 1 to 0.3 and 1 to 3, and the mole ratio of acrolein to acetaldehyde is between 1 to 0.6 and 1 to 4.

12. Composition as claimed in claim 9 wherein the mole ratio of acrolein to formaldehyde is between 1 to 0.01 and 1 to 0.5.

13. Composition as claimed in claim 9 wherein the acid is used in the form of its salt, and such salt is a sodium, potassium or ammonium salt of pentaboric acid, carbonic acid, phosphoric acid, sulfuric acid, hydro-acid, hydrochloric acid, hydrobromic acid, heptamolybdenic acid, formic acid, acetic acid, propionic acid, butyric acid, succinic acid, adipic acid, benzoic acid, phthalic acid, terephthalic acid, nicotinic acid and isonicotinic acid.

* * * * *